United States Patent
Guzman et al.

(10) Patent No.: US 6,849,770 B2
(45) Date of Patent: Feb. 1, 2005

(54) METHOD FOR OBTAINING PURIFIED HYDROXYTYROSOL FROM PRODUCTS AND BY-PRODUCTS DERIVED FROM THE OLIVE TREE

(75) Inventors: Juan Fernandez-Bolaños Guzman, Seville (ES); Antonia Heredia Moreno, Seville (ES); Guillermo Rodriguez Gutierrez, Seville (ES); Rocío Rodriguez Arcos, Seville (ES); Ana Jimenez Araujo, Seville (ES); Rafael Guillen Bejarano, Seville (ES)

(73) Assignee: Consejo Superior de Investigaciones Cientificas, Madrid (ES)

(*) Notice: Subject to any disclaimer, the term of this patent is extended or adjusted under 35 U.S.C. 154(b) by 0 days.

(21) Appl. No.: 10/640,408

(22) Filed: Aug. 13, 2003

(65) Prior Publication Data

US 2004/0102657 A1 May 27, 2004

Related U.S. Application Data

(63) Continuation of application No. PCT/ES02/00058, filed on Feb. 8, 2002.
(51) Int. Cl.$^7$ .............................................. C07C 39/10
(52) U.S. Cl. ...................... 568/763; 424/725; 424/727; 426/655; 574/730
(58) Field of Search ........................ 568/763; 424/725, 424/777; 514/730; 426/655

(56) References Cited

U.S. PATENT DOCUMENTS

| | | | | |
|---|---|---|---|---|
| 6,358,542 B2 | * | 3/2002 | Cuomo et al. ............... | 424/777 |
| 6,416,808 B1 | * | 7/2002 | Crea ........................... | 426/601 |
| 2002/0004077 A1 | | 1/2002 | Cuomo et al. | |
| 2003/0180833 A1 | * | 9/2003 | Espin De Gea et al. ...... | 435/41 |

FOREIGN PATENT DOCUMENTS

IT  1317105  11/2000

OTHER PUBLICATIONS

Andreassi, Marco, Thesis entitled Natural raw materials and their use in the cosmetics, 1999, 3 pages.

* cited by examiner

*Primary Examiner*—Michael L. Shippen
(74) *Attorney, Agent, or Firm*—Klauber & Jackson

(57) ABSTRACT

The present invention relates to a method for obtaining purified hydroxytyrosol from products and by-products derived from the olive tree by means of two-step chromatographic treatment. The invention uses a non-activated ion exchange resin chromatographic method, followed by a second treatment on an XAD-type absorbent non-ionic resin which concentrates and completely purifies the hydroxytyrosol by means of elution with a methanol or ethanol:water dissolution (from 30 to 33%). The method of the invention can also be applied to two-phase pomaces, three-phase pomaces and stones if they are subjected to a steam explosion process.

10 Claims, 1 Drawing Sheet

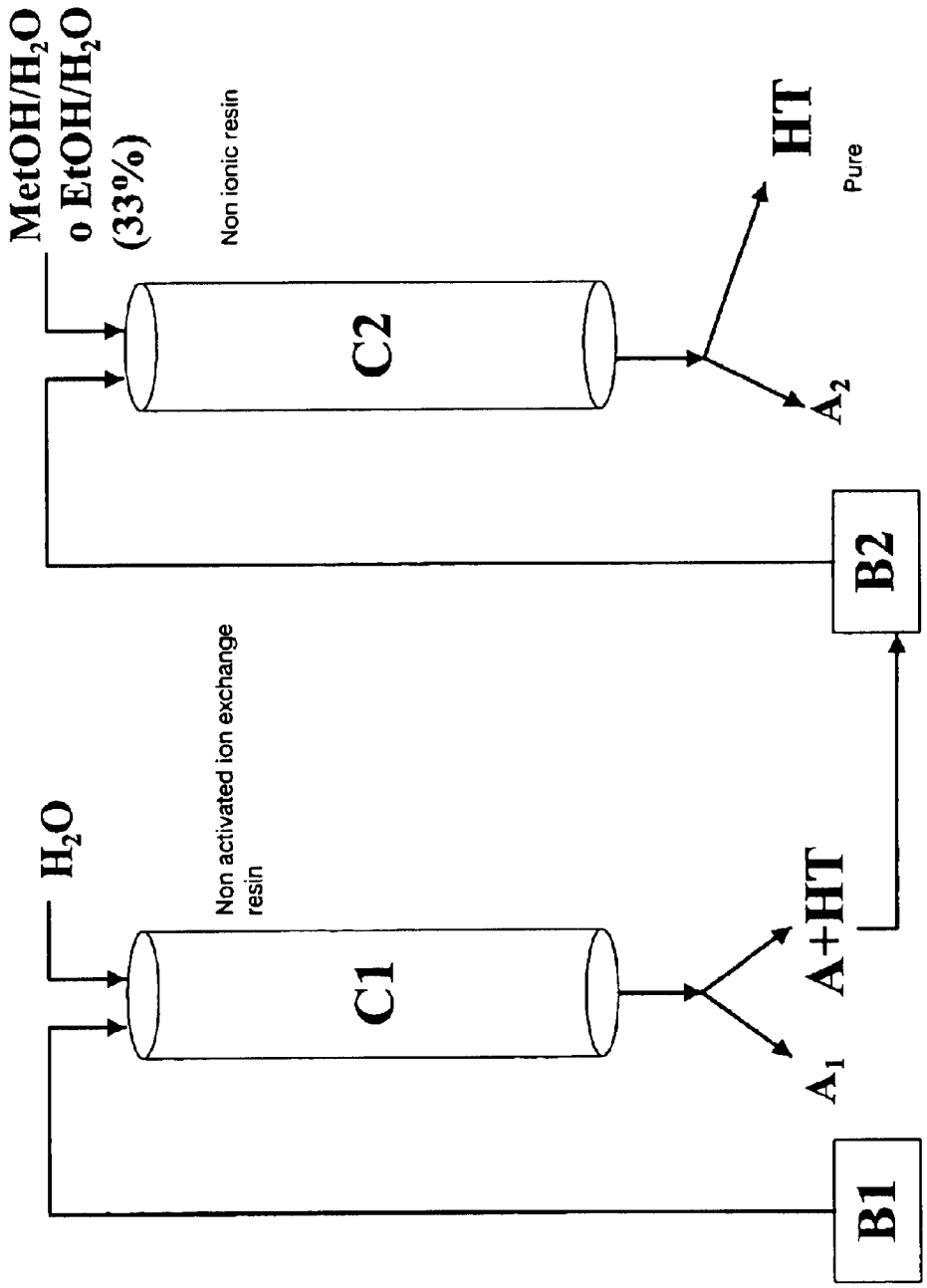

METHOD FOR OBTAINING PURIFIED HYDROXYTYROSOL FROM PRODUCTS AND BY-PRODUCTS DERIVED FROM THE OLIVE TREE

RELATED APPLICATIONS

The present application is a Continuation of co-pending PCT Application No. PCT/ES02/00058 filed Feb. 8, 2002, which in turn, claims priority from Spanish Application Serial No. 200100346, filed Feb. 15, 2001. Applicants claim the benefits of 35 U.S.C. §120 as to the PCT application and priority under 35 U.S.C. §119 as to said Spanish application, and the entire disclosures of both applications are incorporated herein by reference in their entireties.

FIELD OF THE ART

This invention is directed to the food, pharmaceutical, cosmetic and agriculture sectors, the same as the main patent P200002422.

OBJECT OF THE INVENTION

The object of this invention is to improve the method for obtaining purified hydroxytyrosol from products and by-products derived from the olive tree.

Hydroxytyrosol is a natural, high value antioxidant with antimicrobian and phytotoxic properties, which may be used in preserving foodstuff, in agriculture for protecting olive trees and, in addition, advantage may be taken of its prophylactic action in certain human diseases induced by radicals. To this effect, it may be used in various topic preparations, anti-ageing, anti-inflammatory, etc.

The improvements introduced consist in replacing the column of the method's first stage by another, less expensive one with the possibility of re-use, and in eliminating the third purification stage.

STATE OF THE ART

The olive's pulp contains numerous phenolic compounds, almost all in the form of glucoside or its esters, the percentage of which may reach up to 5% of its dry weight. Oleuropeine, the most abundant glucoside, made up by the heteroside ester of elenolic acid and hydroxytyrosol, responsible for its bitter taste, stands out amongst all the phenolic substances. Also present are ligusgtroside (glucose-elenolic acid-tyrosol), verbascoside (caffeic acid-glucose-(rhamnose)-hydroxytyrosol), flavonoides such as rutin and in mature fruits, anthocyanic colorants, derived from cianidine.

All these substances are highly important in the technological processes to which these fruits are subjected, whether for making table olives (e.g., for removing the bitter taste, develop the black colour, etc.) (Brenes, M., Rejano, L., Garcia, P., Sánchez, A. H. and Garrido, A., 1995. J. Agric. Food Chem. 43: 2702–2795) or for obtaining olive oil, since according to their partition coefficient certain phenols pass to the oil and are responsible for stability as against oxidation (Baldioli, M., Servili, M., Perretti, G and Montedoro, G. F., 1996. J. Am. Oil Chem. Soc. 73: 1589–1593), for the sensorial characteristics (Aparicio, R., Roda, L., Albi, M. A. and Gutiérrez, F., 1999. J. Agric. Food Chem. 47: 3531–3534) and for the beneficial effects on human health (Manna, C., Galletti, P., Cucciolla, V., Moltedo, O., Leone, A. and Zappia, V. 1997. J. Nutr. 127: 286–292) and part pass to the aqueous phase.

Hydroxytyrosol, the most active phenol of those found in a natural form in virgin olive oil and fundamentally in its vegetation water or dregs of oil, is spontaneously obtained by chemical and/or enzymatic hydrolisis of oleuropeine during the milling and whipping of pulps. It is also found in very large amounts in liquors and washing water, in view of the chemical hydrolisis occurring in this case, during the making of table olives. It is a very interesting compound because of its antioxidant properties, which owes its activity fundamentally to the odiphenol functional group, characteristic of biophenols, which displays certain very important aspects on human health and preservation of food, apart from playing an important role in defence mechanisms against pathogens and insects in olives (Bianco, A. D., Muzzalupo, I., Piperno, A., Romeo, G. and Ucella, N. 1999. J. Agric. Food Chem. 47:3531–3534).

However, hydroxytyrosol is a product which is not commercially available, despite various chromatographic procedures having been developed for its purification from olive oil, from oil dregs and olive tree leaves and, likewise, several synthesis procedures having been developed for producing it.

Various Italian and Japanese authors have described the recovery of active compounds, mass of phenols from dregs, olive leaves and fruits, with various liquid-liquid and liquid-solid extraction procedures (Visioli, F., Vinceri, F. F. and Galli, C. 1995. Experientia 51: 32–34)(Japanese patent JP-09078061). However, the antioxidant power of the extracts depends on their degree of purification, with the extracts containing low molecular weight phenols being the most active (Violi, F., Romani, A., Mulinacci, N., Zarini, S., Conte, D., Vinceri, F. F. and Galli, C. 1999. J. Agric. Food Chem. 47: 3397–3401).

In relation to the purification of hydroxytyrosol from extracts of oil dregs obtained with ethyl acetate, Capasso et al. 1999 (Capasso, R., Evidente, A., Avolio, S. and Solla, F. 1999. J. Agric. Food Chem. 47: 1745–1748) present a new chromatographic method using columns of silica gel at a medium pressure (20 bar), unlike other previous normal and low pressure extraction and chromatography methods (Capasso, R., Evidente, A. and Visca, C. 1994. Agrochimica 38: 164–171), which are supplemented with fine layer preparative chromatography.

Other Spanish authors (Spanish patent -2051238) obtain different types of phenols, amongst them, hydroxytyrosol, using a counterflow extract from the aqueous solution of the oil dregs. Once the dregs have been extracted as such or concentrated, by a solvent or mixture of solvents not miscible with water, the organic phase is subjected to a counterflow liquid-liquid extraction.

The hydroxytyrosol which has also been purified from olive oil, has been patented for use in topic and bath preparations since it inhibits the formation of melanin and lipid peroxides (Japanese patent JP08119825).

Among the synthesis methods existing, that described by Capasso et al. (Capasso, R., Evidente, A., Avolio, S. and Solla, F. 1999. J. Agric. Food Chem. 47: 1745–1748) is, according to the author himself, the most suitable compared to others described in literature (Baraldi, P. G., Simoni, D., Manfredini, S. and Menziani, E. 1983. Liebigs Ann. Chem. 684–689) and he even points out that that method is even more convenient than the chromatographic recovery the same authors perform from dregs, in view of the low yields of the latter, and that it proves to be much more expensive than those from synthesis. Hydroxytyrosol is synthesised in that paper from 3,4-dihydroxyphenylacetic acid or by reduction with LiAlH4 in tetrahydrofuran, under reflux, for 2 hours.

Bai et al. 1998 (Bai, C., Yan, X., Takenaka, M., Sekiya, K. and Nagata, T. 1998. J. Agric. Food Chem. 46: 3998–4001), also synthesised it with a high yield, on a gram scale, and with high purity. Synthesis is performed from the same 3,4-dihydroxyphenylacetic acid, but using a rapid methylation system with trimethylsildiazomethane and subsequent reduction of the reaction products with NaBH4.

However, the pure acid (analytical purity) used as a raw material in the synthesis methods, is a chemical product with a current price of around 4000 pts/gram which is far too high a price for industrial producing.

Two previous patent applications (ES-9800413 and ES-9800668) show a method for obtaining mannitol from extracted pulp (ES-9800413) from the three phase olive oil extraction system and subjected to a steam explosion process and also a method for obtaining hydroxytyrosol from olive stones (ES9800668) which have been subjected to a rapid self-hydrolysis process. The main patent application (P200002422; dated Jun. 10, 2000) of this invention proposes a method for purifying hydroxytyrosol obtained by the methods referred to or from two phase bagasses (alperujo) also subjected to the steam explosion process. This procedure displays several disadvantages:

- It is unable to totally separate hydroxytyrosol from hydroxymethylfurfural, a degradation compound which increases when severity increases.
- The first column is faced with a strongly coloured solution very rich in various compounds which are retained and, therefore, continuous, strong regenerations become necessary when most of these other compounds remain absorbed in the resin. These regenerations chemically and mechanically alter the resin cutting its useful life. The remaining columns do not have this problem as they are faced with decoloured liquors.
- The resins used are relatively expensive, especially the third column's, although quite resistant.

EXPLANATION OF THE INVENTION

The object of this invention is a method for obtaining purified hydroxytyrosol from products and by-products derived from the olive tree, which includes the following stages:

a) introducing the hydroxytyrosol source in a column with non activated ion exchange resin (preferably a strongly anionic one), and, after water elutriation, obtaining a solution containing at least 85% of the hydroxytyrosol contained in the solution introduced in the column.

b) introducing the solution containing the hydroxytyrosol from the previous stage into a second column of XAD type non ionic resin, and elutriation by means of a methane or ethanol:water mixture (from 30 to 33%), with a solution being obtained containing at least 75% of the hydroxytyrosol contained in the hydroxytyrosol source introduced in the first stage, with minimum purity of 95%.

The resins used in the hydroxytyrosol purification cycles may be regenerated by a treatment consisting of the following stages:

a) in the case of the strongly anionic ion exchange resin, it is regenerated by washing with a strong acid at concentrations around 2N. Should a stronger regeneration be required, after many purification cycles, it would be subjected to prior washing with 2% NaOH before the acid treatment.

b) in the case of XAD type non-ionic resins by washing with methane or pure ethanol or should a stronger regeneration be needed washing with 2% H2O2 with a pH adjusted to 11.5 by adding NaOH.

BRIEF DESCRIPTION OF THE FIGURE

FIG. 1: Diagram of the hydroxytyrosol purification method stages.

DETAILED DESCRIPTION OF THE INVENTION

This invention relates to a chromatograph method enabling hydroxytyrosol with a high degree of purity which has been developed from two and three phase bagasses and from stones from olive processing after being subjected to a steam explosion process to be obtained. Since this is a very severe pre-treatment where the material is subjected to high temperatures by pressurised steam injection for a short period of time, followed by an explosive decompression of the product, hydroxytyrosol and many other water soluble compounds (present in dregs, solubilised products from the bagasse or solid waste, degradation products, etc.) are solubilised. The purification system could also be applied to many other sources, such as dregs, liquors and washing water from preparing olives, etc.

The method of the invention has the use of a two stage chromatographic system as a novelty, using an ionic exchange resin in the first in a non activated form which allows for partial purification of hydroxytyrosol without the latter undergoing any alteration at all, after its elutriation simply with water. These polystyrene based resins can be used in the form of a gel or macroreticular and are easy to regenerate and have great mechanical and functional durability. Their use involves low investment, regeneration and operating costs. The second step is performed on XAD adsorbent polymeric resin enabling the hydroxytyrosol to be completely purified after eluting with a methane) or ethanol:water mixture (from 30 to 33%). This non ionic, polystyrene based resin, which absorbs and releases substances through hydrophobic and polar interactions has the advantage, compared to other resins, that neither retention processes nor important chemical modifications occur to the hydroxytyrosol on the stationary phase. This type of polymeric resins, both the ion exchange one and the adsorbent XAD, are stable to strong acids and strong bases, unlike the silica beds used in other hydroxytyrosol purification methods, they can therefore be used for hundreds of purification cycles, either with acid in the case of the ionic one or methanol or H2O2 (pH=11.5) in the case of the non-ionic.

Regeneration in this method consisted in washing the actual columns themselves with HCl (2N) for the strong anionic one, and with methanol for the adsorbent, to which a fairly clean solution of products arrive and impurify the hydroxytyrosol, and, therefore, drastic regenerations of the latter are not needed.

The purification method's stages are those as shown in the diagram of FIG. 1:

B1: initial sample, source of hydroxytyrosol (aqueous fraction).

C1: non activated ion exchange resin column, hydroxytyrosol is obtained by successive washings with water.

A1: initial sample having now passed through the C1, and washed with water with hardly any hydroxytyrosol.

A2: fraction not retained in the XAD resin, a quite clean solution which could be used as an elutriant in the anionic column.

B2: solution with the compounds, mainly hydroxytyrosol, which are elutriated from the first step by the anionic exchange resin with water, enabling most of the latter to be recovered as it has a different drag speed through the resin bed than the rest of the compounds accompanying it.

C2: chromatography on adsorbent XAD resin enabling the hydroxytyrosol to be concentrated and totally purified by means of elutriation with a mixture of methane) or ethanol:water (from 30 to 33%). PURE HT: pure hydroxytyrosol.

MODE OF CARRYING OUT THE INVENTION

The purification method was developed from a sample of bagasse subjected to a steam explosion process. About 2 Kg of bagasse (with about 8.5 g of hydroxytyrosol) are subjected to a steam explosion process. Steam under pressure is injected into a reactor for 10 minutes at a temperature of 190–220° C., in the presence of 2.5% H2SO4 p/v; when the material explosively decompresses, apart from a certain chemical reaction, it undergoes major destructuring and part thereof is solubilised. After separating the soluble and insoluble fractions, the first is taken, and there remains a 0.5 g/L concentration of hydroxytyrosol, which has to be purified in two steps:

1st step: Sample (B1) is placed in the first column (C1) with 1.25 Kg of strong non-activated anionic resin. The liquor collected at the outlet of the column displays the same colour as the initial sample and, therefore, all the hydroxytyrosol and little else is retained in the column. Washings are performed with water until 80% of the hydroxytyrosol introduced is recovered, about 7 g, and a dry extract with a richness of 60% of hydroxytyrosol is obtained.

2nd step: the water washings which have dragged away the 7 g of hydroxytyrosol (B2) are introduced into the column (C2) with 1.5 Kg of XAD resin. The hydroxytyrosol is retained and is finally elutriated with a 33% mixture of methanol and water. A concentrated hydroxytyrosol solution (CONC HT) is thus obtained containing 6.5 g of hydroxytyrosol with a purity of at least 95% and a concentration of 2.2 g/L. Purification can be performed more or less completely according to the aims of the material it is endeavoured to obtain with the method of the invention.

The non retained fraction in the first column, fraction (A1), can be used to obtain mannitol (31 g) and other sugars, amongst them glucose (82 g) stands out.

What is claimed is:

1. Method for obtaining purified hydroxytyrosol from products and by-products derived from the olive tree, characterized in that it comprises the following stages:
   a) introducing the hydroxytyrosol source into a column of non-activated, ion exchange resin and, after elutriation with water, obtaining a solution containing at least 85% of the hydroxytyrosol present in the source of hydroxytyrosol introduced in the column, therewith obtaining 60–70% rich hydroxytyrosol,
   b) introducing the solution containing hydroxytyrosol from the previous stage into a second column of non ionic resin and subsequent elutriation with a mixture of methanol or ethanol:water (from 30 to 33%), obtaining a solution containing at least 75% of the hydroxytyrosol present in the source of hydroxytyrosol introduced in the first stage with a minimum purity of 95%.

2. Method for obtaining purified hydroxytyrosol from products and by-products derived from the olive tree according to claim 1, characterized in that prior to the treatment in the columns of resin, the source of hydroxytyrosol is subjected to a steam explosion process.

3. Method for obtaining purified hydroxytyrosol from products and by-products derived from the olive tree according to claim 1, characterized in that the column of non-activated ion exchange resin is a column with strong anionic exchange resin.

4. Method for obtaining purified hydroxytyrosol from products and by-products derived from the olive tree according to claim 2, characterized in that the column of non-activated ion exchange resin is a column with strong anionic exchange resin.

5. Method for obtaining purified hydroxytyrosol from products and by-products derived from the olive tree according to claim 1, characterized in that the non ionic column is an Amberite XAD resin column.

6. Method for obtaining purified hydroxytyrosol from products and by-products derived from the olive tree according to claim 2, characterized in that the non ionic column is an Amberite XAD resin column.

7. Method for obtaining purified hydroxytyrosol from products and by-products derived from the olive tree according to claim 3, characterized in that after the purifying cycles, the anionic exchange resin is regenerated by a treatment consisting of the following stages:
   a) washing with 2% NaOH
   b) washing with strong acid.

8. Method for obtaining purified hydroxytyrosol from products and by-products derived from the olive tree according to claim 4, characterized in that after the purifying cycles, the anionic exchange resin is regenerated by a treatment consisting of the following stages:
   a) washing with 2% NaOH
   b) washing with strong acid.

9. Method for obtaining purified hydroxytyrosol from products and by-products derived from the olive tree according to claim 5, characterized in that after the purifying cycles, the XAD adsorbent resin is regenerated by a treatment consisting in the following stages:
   a) extraction of all the hydroxytyrosol accompanying compounds retained in the resin, with methane or ethanol in the same column, or hot extraction by using soxhlet.
   b) washing with a solution of 2% $H_2O_2$ with pH adjusted to 11.5 by adding NaOH.

10. Method for obtaining purified hydroxytyrosol from products and by-products derived from the olive tree according to claim 6, characterized in that after the purifying cycles, the XAD adsorbent resin is regenerated by a treatment consisting in the following stages:
   a) extraction of all the hydroxytyrosol accompanying compounds retained in the resin, with methane or ethanol in the same column, or hot extraction by using soxhlet.
   b) washing with a solution of 2% $H_2O_2$ with pH adjusted to 11.5 by adding NaOH.

* * * * *

UNITED STATES PATENT AND TRADEMARK OFFICE
CERTIFICATE OF CORRECTION

PATENT NO.   : 6,849,770 B2
DATED         : February 1, 2005
INVENTOR(S)  : Juan Fernadez-Bolanos Guzman et al.

It is certified that error appears in the above-identified patent and that said Letters Patent is hereby corrected as shown below:

<u>Title page,</u>
Item [30], Foreign Application Priority Data, please add -- Spanish Application No. 200100346, filed February 15, 2001 --

Signed and Sealed this

Fifth Day of July, 2005

JON W. DUDAS
*Director of the United States Patent and Trademark Office*